United States Patent [19]

Duffett et al.

[11] Patent Number: Plant 6,059

[45] Date of Patent: Dec. 8, 1987

[54] CHRYSANTHEMUM PLANT NAMED ADORN

[75] Inventors: William E. Duffett; Cornelis P. VandenBerg, both of Salinas, Calif.; Grace H. Mack, 108 Wahackme Rd., New Canaan, Conn. 06840

[73] Assignee: Grace H. Mack, New Canaan, Conn.

[21] Appl. No.: 767,360

[22] Filed: Aug. 20, 1985

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Adorn having flat capitulum form; daisy capitulum type; purple ray floret color; diameter across face of capitulum up to 8 cm.; short plant height; semi-spreading branching pattern; average natural season flowering date of September 10 in the West Coast area; average flowering response period of seven weeks in photoperiodic controlled short day programs; and durable, uniform performance in Spring small pot flowering programs.

3 Drawing Figures

1

The present invention comprises a new and distinct cultivar of *Chrysanthemum morifolium,* Ramat., named Adorn.

Adorn is a product of a planned breeding program which had the objective of creating new Chrysanthemum cultivars with daisy capitulum type, short plant height, spreading branching pattern, durable inflorescence, six to seven week flowering response period, and purple ray floret color under outdoor natural season conditions.

Adorn, identified as 82N11009, was originated from a cross made by Grace H. Mack in a controlled breeding program in New Canaan, Conn. in the year 1981. The female parent was an unnamed seedling bred from Wolverine, disclosed in U.S. Plant Pat. No. 4,312, crossed with M720, an unnamed seedling. The male parent was M520, unnamed, derived from two unnamed seedlings.

Adorn was discovered and selected as a flowering plant within the progeny of the stated cross by William E. Duffett in September 1982 in a controlled open area in Salinas, Calif.

The first act of asexual reproduction of Adorn was accomplished when vegetative cuttings were taken from the initial selection in February 1983 by Cornelis P. VandenBerg. Horticultural examination of selected units initiated October 1983 has demonstrated that the combination of characteristics as herein disclosed for Adorn are firmly fixed and are retained through successive generations of asexual reproduction.

Adorn has not been observed under all possible environmental conditions. The phenotype may vary significantly with variations in environment such as temperature, light intensity and day length. The observations, measurements and comparisons describe plants grown in a controlled open area in Salinas, Calif.

Rooted cuttings were established in soil and maintained outdoors under the natural temperature and day length prevailing during July and September. Single pinching was practiced with all branches and buds retained.

The following traits have been repeatedly observed and are determined to be basic characteristics of Adorn, which in combination distinguish this Chrysanthemum as a new and distinct cultivar:

2

(1) Flat capitulum form.
(2) Daisy capitulum type.
(3) Purple ray floret color.
(4) Diameter across face of capitulum up to 8 cm.
(5) Short plant height.
(6) Semi-spreading branching pattern.
(7) Average natural season flowering date of September 10.
(8) Average flowering response of seven weeks in photoperiodic controlled flowering programs.
(9) Durable, uniform performance in Spring, small pot flowering programs.

The accompanying photographic drawings show typical leaf and inflorescence characteristics of Adorn.

Sheet 1 is a color photograph of Adorn.

Sheet 2 is a black and white photograph of three views of the inflorescence of Adorn.

Sheet 3 is a black and white photograph showing the leaves of Adorn in three stages of growth (mature, intermediate and immature).

Of the many commercial cultivars known to the present inventors, the most similar in comparison to Adorn is Stardom, disclosed in U.S. Plant Pat. No. 3,530. Reference is made to attached Chart A which compares certain characteristics of Adorn to those same characteristics of Stardom. Similar traits are type, form, plant height, durability of form and color, and response. Adorn differs from Stardom by its deeper color, earlier natural season flower date, less spreading habit and larger diameter across the face of the capitulum.

In the following description, color references are made to The Royal Horticultural Society Colour Chart. The color values were determined between 2:15 and 2:30 p.m. on Sept. 14, 1984 under 380 foot-candle light intensity at Salinas, Calif.

Classification:

*Botanical.*—*Chrysanthemum morifolium,* Ramat., cv Adorn.

*Commercial.*—Daisy spray pot mum and garden cultivar.

INFLORESCENCE

A. Capitulum:

*Form.*—Flat.

*Type.*—Daisy.

*Permanence.*—Approximately 14 days.

*Diameter across face.*—6 to 8 cm.

B. Corolla of ray florets:

*Color (General tonality from a distance of three meters).*—Purple.

*Color (upper surface).*—between 78B and 78C.

*Color (under surface).*—between 78C and 78D.

*Shape.*—Long and narrow. Rounded tip. Ligulate, spoon and tubular.

C. Corolla of disc florets:

*Color (mature).*—3B.

*Color (immature).*—154C.

D. Reproductive organs:

*Androecium.*—Present disc florets; abundant pollen.

*Gynoecium.*—Present both ray and disc florets.

PLANT

A. General appearance:

*Height.*—Short.

*Branching pattern.*—Semi-spreading.

B. Foliage:

*Color (upper surface).*—147A.

*Color (under surface).*—147B.

*Shape.*—Broad and deeply lobed. Very slight serration.

CHART A

COMPARISON OF ADORN AND STARDOM

| RAY | CAPITULUM | AVERAGE SEASON |
|---|---|---|

CHART A-continued

COMPARISON OF ADORN AND STARDOM

| CULTIVAR | FLORET COLOR | FORM AND TYPE | FLOWER DATE | PLANT HEIGHT |
|---|---|---|---|---|
| ADORN | PURPLE | FLAT DAISY | SEPTEMBER 10 | SHORT |
| STARDOM | LIGHT LAVENDER | FLAT DAISY | SEPTEMBER 20 | SHORT |

| CULTIVAR | BRANCHING PATTERN AND SPREAD | DIAMETER ACROSS FACE OF CAPITULUM | PERMANENCE OF FORM AND COLOR | CONTROLLED RESPONSE |
|---|---|---|---|---|
| ADORN | SEMI-SPREADING | 6 to 8 cm. | 14 DAYS | SEVEN WEEKS |
| STARDOM | SPREADING | 5 to 6 cm. | 10–14 DAYS | SEVEN WEEKS |

COMPARISONS MADE OF PLANTS GROWN UNDER NATURAL SEASON OUTDOOR CONDITIONS IN SALINAS, CALIFORNIA

We claim:

1. A new and distinct cultivar of *Chrysanthemum morifolium,* Ramat., named Adorn, as described and illustrated, and particularly characterized as to uniqueness by the combined characteristics of flat capitulum form, daisy capitulum type, purple ray floret color, diameter across face of capitulum up to 8 cm., short plant height, semi-spreading branching pattern, average natural season flowering date of September 10 in the West Coast area, average flowering response period of seven weeks in photoperiodic controlled short day programs, and durable, uniform performance in Spring small pot flowering programs.

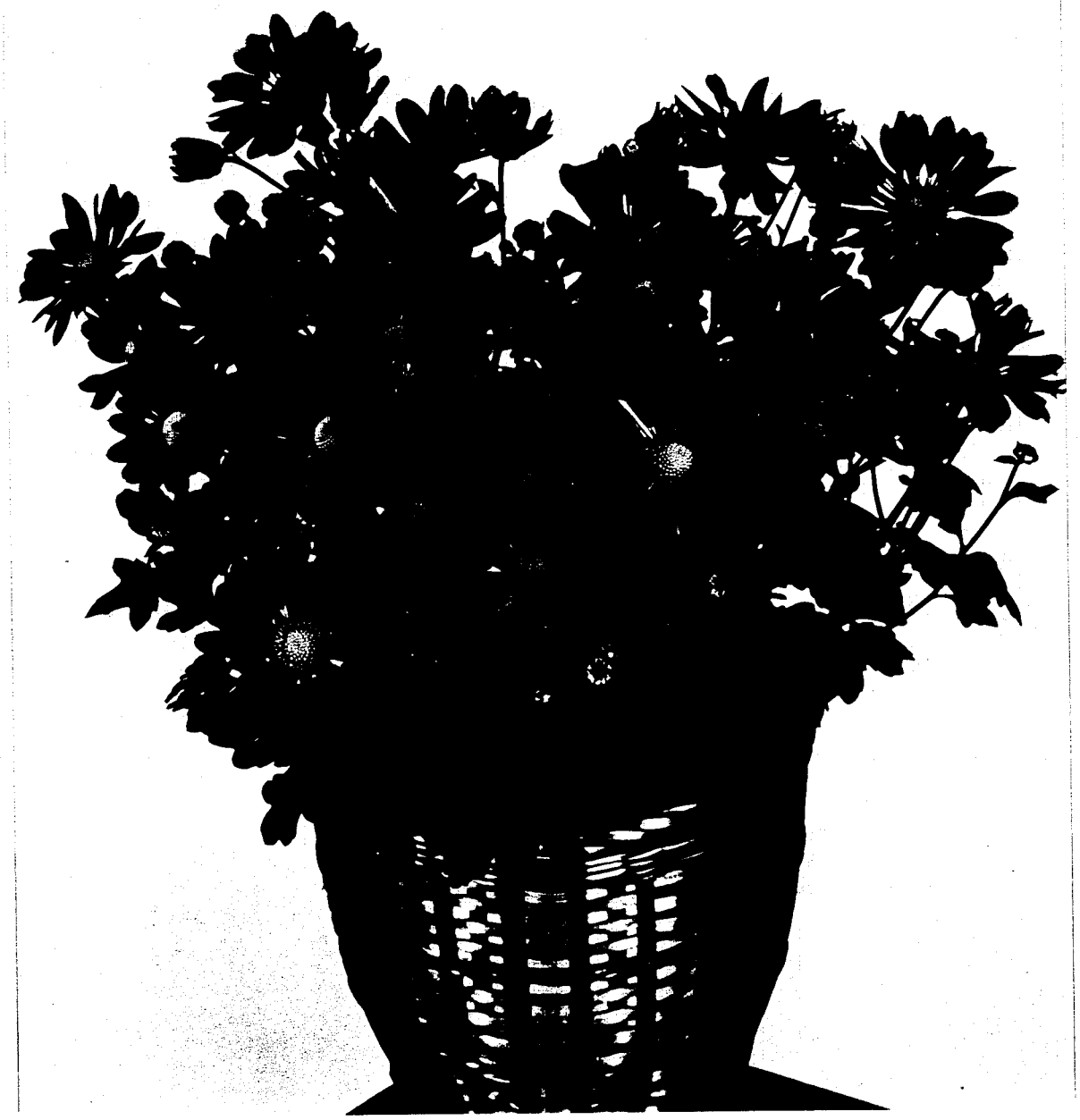

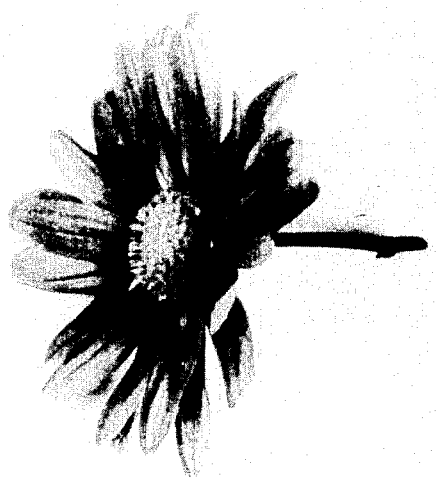
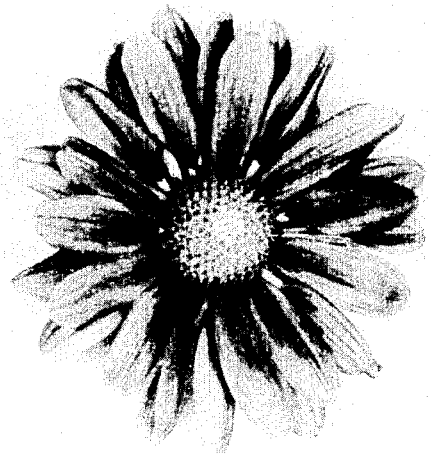
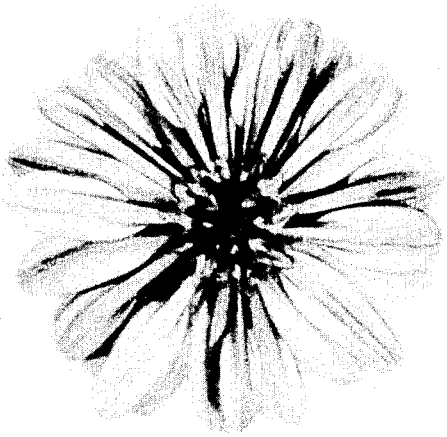

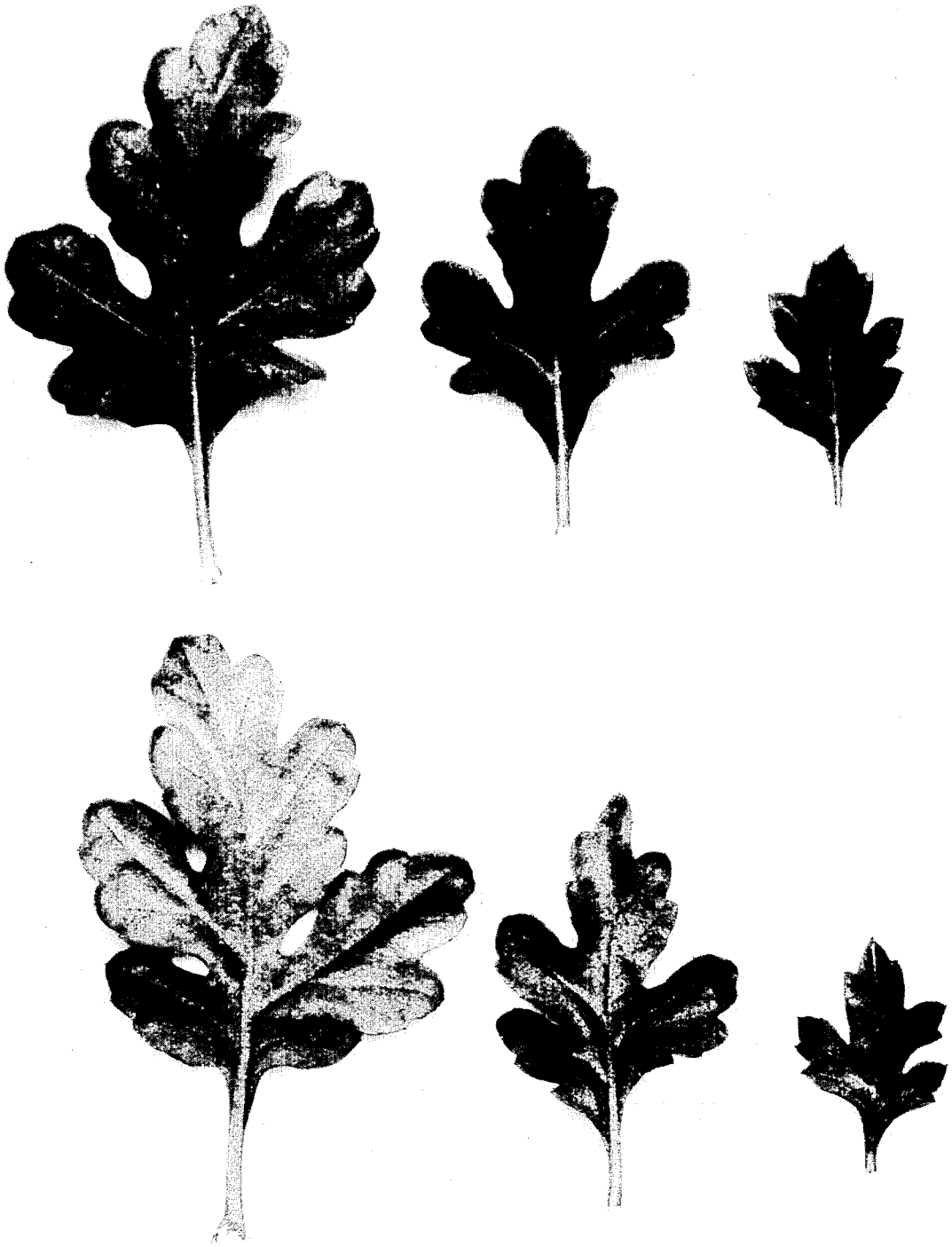

* * * * *